United States Patent
Stroud

(10) Patent No.: US 8,202,210 B2
(45) Date of Patent: *Jun. 19, 2012

(54) ARTIFICIAL BREEDING TECHNIQUES FOR BOVINES INCLUDING SEMEN DILUENTS AND AI APPARATUS

(76) Inventor: Brad K. Stroud, Weatherford, TX (US)

( * ) Notice: Subject to any disclaimer, the term of this patent is extended or adjusted under 35 U.S.C. 154(b) by 1278 days.

This patent is subject to a terminal disclaimer.

(21) Appl. No.: 11/829,240

(22) Filed: Jul. 27, 2007

(65) Prior Publication Data

US 2009/0030268 A1 Jan. 29, 2009

(51) Int. Cl.
*A61D 19/02* (2006.01)
*A61D 7/00* (2006.01)

(52) U.S. Cl. .......................................... 600/35; 600/33

(58) Field of Classification Search ............... 600/33–35
See application file for complete search history.

(56) References Cited

U.S. PATENT DOCUMENTS

| | | |
|---|---|---|
| 2,566,632 A | 9/1951 | Propp |
| 3,256,884 A | 6/1966 | Hill et al. |
| 3,811,423 A | 5/1974 | Dickinson, III et al. |
| 3,811,443 A | 5/1974 | Dickinson, III et al. |
| 3,877,430 A | 4/1975 | Wieder |
| 3,889,676 A | 6/1975 | Greene |
| 3,910,275 A | 10/1975 | Babey et al. |
| 4,301,797 A | 11/1981 | Pollack |
| 4,305,392 A | 12/1981 | Chester |
| 4,324,235 A | 4/1982 | Beran |
| 4,335,723 A | 6/1982 | Patel |
| 4,419,986 A | 12/1983 | Leibo |
| 4,457,313 A | 7/1984 | Alter |
| 4,493,700 A | 1/1985 | Cassou et al. |
| 4,654,025 A | 3/1987 | Cassou et al. |
| 4,780,451 A * | 10/1988 | Donaldson ..................... 514/9.9 |
| 5,030,202 A | 7/1991 | Harris |
| 5,147,299 A | 9/1992 | Mendoza et al. |
| 5,496,272 A | 3/1996 | Chung et al. |
| 5,904,665 A | 5/1999 | Muharib |
| 5,916,144 A | 6/1999 | Li et al. |
| 5,985,538 A | 11/1999 | Stachecki |
| 6,071,231 A | 6/2000 | Mendoza et al. |

(Continued)

FOREIGN PATENT DOCUMENTS

CA 1073286 3/1980

(Continued)

OTHER PUBLICATIONS

Wiggins et al. "Minimal Volume of Semen and Number of Sperm for Fertility in Artificial Insemination of Swine." Journal of Animal Science 10.1 (1951):138-143. Web. Aug. 16, 2011.*

(Continued)

*Primary Examiner* — Charles A Marmor, II
*Assistant Examiner* — Carrie R Dorna
(74) *Attorney, Agent, or Firm* — Husch Blackwell LLP

(57) ABSTRACT

In the preferred embodiment, bovine semen is mixed with a suitable solution to form an insemination medium which is injected into the reproductive organs of a female bovine to flood the uterine horns in a nonsurgical AI procedure. The invention includes an AI instrument having a disposable, single use pipette that may be used with this nonsurgical procedure. The AI instrument does not include a balloon and is referred to as "catheter free". Preferably, the uterine horns are flooded concurrently, but in the alternative, they may be flooded sequentially.

20 Claims, 4 Drawing Sheets

U.S. PATENT DOCUMENTS

| | | | |
|---|---|---|---|
| 6,130,034 | A | 10/2000 | Aitken |
| 6,140,121 | A | 10/2000 | Ellington et al. |
| 6,368,786 | B1 | 4/2002 | Saint-Ramon et al. |
| 6,454,756 | B1 | 9/2002 | Sasaki |
| 6,551,236 | B1 | 4/2003 | Liegois |
| 7,056,279 | B2 | 6/2006 | Verberckmoes et al. |
| 7,339,090 | B2 | 3/2008 | Christmann |
| 2004/0199044 | A1* | 10/2004 | Verberckmoes et al. ....... 600/35 |

FOREIGN PATENT DOCUMENTS

| | | |
|---|---|---|
| EP | 0071538 | 9/1983 |
| EP | 0071538 | 6/1985 |
| EP | 0538786 | 4/1993 |
| EP | 0685556 | 6/1995 |
| FR | 2647668 | 12/1990 |
| FR | 2720407 | 1/1995 |
| FR | 2720407 | 12/1995 |
| GB | 867274 | 5/1964 |

OTHER PUBLICATIONS

Amann, Rupert P., Exposure of Thawed Frozen Bull Sperm to a Synthetic Peptide Before Artificial Insemination Increases Fertility, Journal of Andrology, (1999), 42-46, vol. 20, No. 1.

Barth, AD, Factors Affecting Fertility with Artificial Insemination, Vet. Clin. North Am. Food Anim. Pract. (1993), 275-89, 9(2).

Berber, et al., Comparison of Two Ovsynch Protocols (Gnrh Versus LH) for Fixed Timed Insemination in Buffalo (*Bubalus bubalis*), Theriogenology (2002), 1421-30, 57(5).

Bergqvist, Ann-Sofi, et al, Sulphated Glycosaminoglycans (S-GAGs) and Syndecans in the Bovine Oviduct, Animal Reproduction Science 93, (2006) 46-60.

Betteridge, K.J., An Historical Look at Embryo Trnasfer, J. Reprod. Fert., (1981), 62, 1-13.

Block, J., et al., Effect of Addition of Hyaluronan to Embryo Culture Medium on Survival of Bovine Embryos in Vitro Following Vitrification and Establishment of Pregnancy After Trasnfer to Recipients, Theriogenology, (2009), on-line publication of 9 pages.

Brackett, Benjamin G., Fertilization and Early Development of Cow Ova, Biology of Reproduction 23 (1980), 189-205.

Dairy Herd Staff, Reproductive Efficiency = Environmental Efficiency, Dairy Herd Management, (2009).

Dalton et al., Effect of a Deep Uterine Insemination on Spermatozoal Accessibility to the Ovum in Cattle: A Competitive Insemination Study, Theriogenology (1999), 883-890, vol. 51, Iss. 5.

Dalton, Jospeh C., Factors Important to the Efficiency of Artificial Insemination in Single-Ovulating and Superovulated Cattle, Dissertation submitted for degree of Doctor of Philosophy in Animal Science, (1999).

DeJarnette, J.M., et al., Accessory Sperm: Their Importance to Fertility and Embryo Quality, and Attempts to Alter Their Numbers in Artificially Inseminated Cattle, J. Anim Sci, (1992), 70:484-491.

Foote, R.H., The History of Artificial Insemination: Selected Notes and Notables, American Society of Animal Science, (2002), 1-10.

Furmus, et al, Effect of Hyaluronic Acid on Development of In Vitro Produced Bovine Embryos, Centro de Investigaciones Reproductivas Pérez Companc, Theriogenology (1998), 49:1489-1499.

Gao, Q.H, et al., Successful Low Dose Insemination of Flow Cytometrically Sorted Sika (*Cervus nippon*) Sperm in Wapiti (*Cervus elaphus*), Animal Reproduction Science, (2009).

George, F., et al., Set Up of a Serum-Free Culture System for Bovine Embryos: Embryo Development and Quality Before and After Transient Transfer, Theriogenology 69, (2008), 612-623.

Graves, et al., Evaluation of Uterine Body and Bilteral Uterine Horn Insemination Techniques, J. Dairy Sci. (1991) 3454-6, 74(10).

Hawk, H.W., Transport and Fate of Spermatozoa After Insemination of Cattle, Journal of Dairy Science , (1987), pp. 1487-1503, vol. 70, No. 7.

Hawk, H.W., et al, Effect of Unilateral Cornual Insemination upon Fertilization Rate in Superovulating and Single-Ovulating Cattle, J Anim Sci, (1986), 63:551-560.

Hawk, H.W., Sperm Survival and Transport in the Female Reproductive Tract, J Dairy Sci (1983) 66:2645-2660.

Heiskanen et al., Insemination Results with Slow-Cooled Stallion Semen Stored for 70 or 80 Hours, Theriogenology (1994), 1043-1051, vol. 42., Iss. 6.

Hunter, RH; Advances in Deep Uterine Insemination: A Fruitful Way Forward to Exploit New Sperm Technologies in Cattle, Anim Reprod Sci., (2003) 157-170, 79(3-4).

Hunter et al., Deep Uterine Insemination of Cattle: A Fruitful Way Forward with Smaller Numbers of Spermatozoa, Acta Vet Scand. (1998), 149-63, 39(2.

Hunter, R.F.H., et al., Sperm Transport in the Cow: Periovulatory Redistribution of Viable Cells Within the Oviduct, Reprod. Nutr Develop., 24: (1984), 597-608.

Januskauskas, A., et al, Relationship Between Sperm Response to Glycosaminoglycans In Vitro and Non-Return Rates of Swedish Dairy AI Bulls, Reprod Dom Anim 35, (2000), 207-212.

Kurykin, et al., Fixed Time Deep Intracornual Insemination of Heifers at Synchronized Estrus, Theirogenology (2003), 1261-8; 60(7).

López-Gatius, F., et al., Intraperitoneal Insemination and Retrograde Sperm Transport in Dairy Cows, J. Vet. Med. A 47, (2000), 83-88.

Mitchell, J.R., Distribution and Retention of Spermatozoa with Acrosomal and Nuclear Abnormalities in the Cow Genital Tract, J. Amin. Sci., (1985), 61:956-967.

Munkittrick, T.W., Accessory Sperm Numbers for Cattle Inseminated with Protamine Sulfate Microcapsules, J. Dairy Sci. (1992), 75:725-731.

Nebel, et al, Microencapsulation of Bovine Spermatozoa for Use in Artificial Insemination: A Review, Reproduction, Fertility and Development (1993), 701-712, 5(6).

Nebel et al, Microencapsulation of Bovine Spermatozoa, J. Anim Sci (1985), 60:1631-1639.

Niżański, Wojciech, Intravaginal Insemination of Bitches with Fresh nd Frozen-Thawed Semen with Addition of Prostatic Fluid: Use of an Infusion Pipette and the Osiris Catheter, Theriogenology, (2006), 470-483, vol. 66, Iss. 2.

Palasz, A.T., et al., Effects of Hyaluronan, BSA, and Serum on Bovine Embryo In Vitro Development, Ultrastructure, and Gene Expression Patterns, Molecular Reproduction and Development (2006), 73:1503-1511.

Peippo. J. et al., Embryo Production From Superovulated Holstein-Friesian Dairy Heifers and Cows After Insemination With Frozen-Thawed Sex-Sorted X Spermatozoa or Unsorted Semen, Anim Reprod Sci. (2009), 111(1): 80-92.

Peña, F.J., et al., Effect of Hyaluronan Supplementation on Boar Sperm Motility and Membrane Lipid Architecture Status After Cryoperservation, Theriogenology 61 (2004), 63-70.

Ranganathan, Sripriya et al, Evidence for Presence of Hyaluronan Binding Protein on Spermatozoa and Its Possible Involvement in Sperm Function, Molecular Reproduction and Development (1994) 38:69-76.

Rodriguez-Martinez, H., Role of the Oviduct in Sperm Capacitation, Theriogenology 68S, (2007), S138-S146.

Saacke, R.G., et al., Involvement of the Bull and Inseminate in Fertility and Embryo Quality, AET Convention, (1994), 43-55.

Saacke, R.G., What Happens to All Those Sperm?: The Interation of Male and Female in Success of Mating, Theriogenology (2004), Lexington, KY.

Salisbury, G.W., et al., Preservation of Bovine Spermatozoa in Yolk-Citrate Diluent and Field Results From Its Use, Journal of Dairy Science, (1941), 905-910, vol. XXIV, No. 11.

Salisbury, G.W., et al., Further Studies of the Effect of Dilution Rate on the Fertility of Bull Semen Used for Artificial Insemination, (1944) 233-241.

Salisbury, G.W., Fertility of Bull Semen Diluted at 1:100, J. Dairy Sci. (1946), 695-697.

Salisbury, G.W., et al., Fertility Level of Bull Semen Diluted at 1:400 With and Without Sulfanilamide, (1948), 817-822.

Schenk, J.L., et al., Effects of Extender and Insemination Dose on Postthaw Quality and Fertility of Bovine Sperm, J Dairy Sci 70 (1987), 1458-1464.

Sieme, et al., Effects of Different Artificial Insemination Techniques and Sperm Doses on Fertility of Normal Mares and Mares with Abnormal Reproductive History, Theriogenology, (2004), 915-928, vol. 62, Iss. 5.

Sirard, M.-A, et al., In Vivo and In Vitro Effects of FSH on Oocyte Maturation and Developmental Competence, Theriogenology 68S, (2007) S71-S76.

Suarez, S.S., Interactions of Spermatozoa with the Female Reproductive Tract: Inspiration for Assisted Reproduction, Reproduction, Fertility and Development, (2007), 19, 103-110.

Talbot, Prudence, et al., Cell Adhesion and Fertilization: Steps in Oocyte Transport, Sperm-Zona Pellucida Interactions, and Sperm-Egg Fusion, Biology of Reproduction 68, (2003), 1-9.

Tanabe, T.Y., The Nature of Reproductive Failure in Cows of Low Fertility, Wisconsin Agricultrual Experiment Station, (1948), Paper No. 383, 237-246.

* cited by examiner

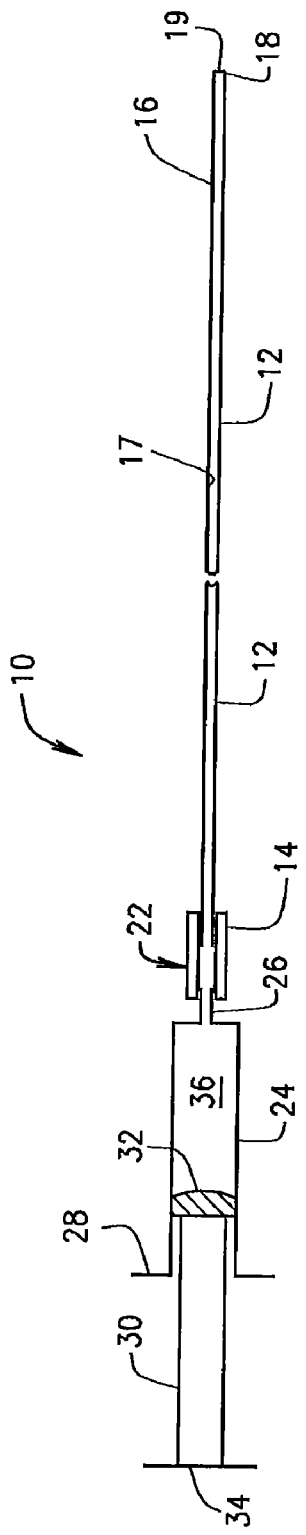
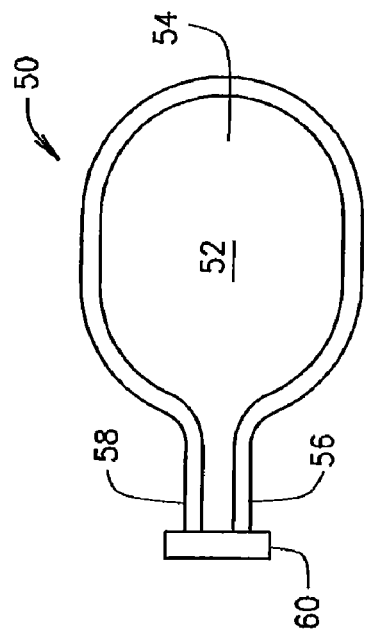

ARTIFICIAL BREEDING TECHNIQUES FOR BOVINES INCLUDING SEMEN DILUENTS AND AI APPARATUS

BACKGROUND OF THE INVENTION

Various artificial breeding techniques have been developed for mammals and specifically bovines, including artificial insemination ("AI") and embryo transfer ("ET").

Various breeds of cattle are often bred for specific purposes. For example, Angus, Brahman, Charolais, Hereford, Polled Hereford and Simmental are often bred for beef production. Holstein, Jersey, Guernsey, Ayrshire and Brown Swiss are often bred for the dairy industry. The following discussion is intended as background on cattle in general and this data may vary depending on the specific breed, food availability or the lack thereof and the weather.

In a natural setting, cows, heifers and at least one bull are free to roam in a pasture. The gestation for bovines is about 9 months. After a calf is born, there is a delay of 2 or 3 months before the cow will come into heat (estrus). Heifers may have an even longer rebreeding delay. This delay in rebreeding allows the cow to produce milk for the new calf and bring hormones back to normal levels. After this delay (postpartum anestrous) the cow will usually come into heat every 18-24 days, unless interrupted by pregnancy or some problem.

Cows have two ovaries, but in the natural setting only one egg will be released from one ovary during each estrous cycle. The egg will travel down the respective oviduct. During heat, the cow is sexually attractive to both bulls and cows and will stand firm when other animals attempt to mount her. During heat, the three fibrous rings in the cow's cervix relax. Therefore when a bull mates with a cow in heat, his penis passes through the vulva, the posterior vagina, and the anterior vagina to a point very near the external cervical os. When the bull ejaculates, approximately 4-9 billion sperm are injected into the anterior vagina. Some of these sperm are transported through folds in the lining of the uterine horns (endometrium) of the uterus and into the oviducts. Conception occurs in the oviducts. The fertilized egg travels down the oviduct and embeds itself in the horn of the uterus where it develops until birth.

Conception rates for natural sexual breeding are very high because of the high number of sperm that are ejaculated per intercourse and because the bull will typically mate the cow or heifer on multiple occasions while she is in heat.

As previously mentioned, cattle are raised for a number of different purposes including dairy cattle, beef cattle, rodeo cattle, and seed cattle which are used to build a herd. The lifespan of cattle varies depending on the goals of the rancher. For example, beef cattle reach maturity in two to three years, but may be slaughtered after they reach a sufficient weight in 15-20 months. In the dairy industry, female calves from the best cows are saved for herd replacement, and bull calves are usually sold at a few days of age to be eventually slaughtered for beef. Mature dairy females are often slaughtered after 3 or 4 years of milk production. But beef seed stock cattle and rodeo cattle may have substantially longer lives to increase the number of high quality calves that are produced per cow. Left in a natural setting and well managed with adequate food and water, cattle will produce on average about one calf per year. Assuming the cow lives 10 years, and gives birth to her first calf in the second year of life, the average beef cow will produce about 7 to 8 calves over her lifespan. The average dairy cow will only produce about 2 to 3 calves in her lifetime due to the stresses of high lactation output.

To increase the value of a cow's calves beef cattle ranchers and dairymen utilize frozen semen from the most valuable bulls in the industry to breed their cows. Since frozen semen can be shipped commercially around the world, the best bulls can be mated to thousands of cows instead of the usual 20 to 40 under natural pasture mating conditions.

Cryopreservation techniques for semen are well known to those skilled in the art and will be briefly summarized. About 5 ml to about 15 ml of semen is collected from a bull after being electroejaculated. The semen is mixed with a suitable extender and cryoprotectant. Assuming about 10 ml of semen have been collected, it may be mixed with about 240 ml of Triladyl® solution, which is an off the shelf product that is available from Minitube of America in Verona, Wis. (www.minitube.com) The Triladyl contains and extender and a cryoprotectant, such as glycerol. The mixture of semen, extender and cryoprotectant is then placed in plastic straws and frozen. In the industry the contents of the frozen straw is generally referred to as frozen semen, although is also contains an extender and a cryoprotectant. The goal is to cryopreserve about 20 million motile sperm in a ½ ml semen straw.

Artificial insemination (AI) is the process whereby frozen semen is thawed, placed in a AI instrument, and manually passed through the vagina, then the cervix and ultimately into the body of the uterus where it is deposited. Only a drop or two of semen is typically used per prior art AI session. Semen straws contain about ¼ or ½ ml of fluid and typically only one or two straws are used per prior art AI session. To increase the number of calves that a valuable cow can produce, embryo transfer (ET) techniques have been developed and are well know to those skilled in the art. Conventional embryo transfer techniques include injection of genetically valuable cows with suitable hormones which cause them to produce multiple eggs (oocytes) in a single estrous cycle. This process is often referred to as superovulation. Each cow is then artificially inseminated with semen from a valuable bull that has been cryopreserved using conventional cryopreservation techniques.

Once inseminated with semen, some of the oocytes become fertilized, which are then referred to as embryos. However, many of the eggs are not fertilized or they die shortly after The diluted semen is then loaded into the inseminating pipette by aspirating it out of the ampoule, whereupon it is pushed with air from a syringe out of the distal end of the pipette into the uterus of the animal through the anchored tip which is sealed against the cervix to prevent the fluid from leaking back.

Mendoza '231 describes the process of the second patent as follows, beginning at Column 4, line 60: "With the aid of a plastic lighted speculum 32 to open the animal's vagina and view the interior, the device 29 is pressed part way into the cervix 33, the balloon 24 is inflated to form a seal with the cervix, and the dilution fluid is forced out of the syringe, pushing the semen sample and diluent into the uterus 34." The dilution fluid 17 is described as 2.9% sodium citrate dilution fluid at Col. 3, line 58.

In Mendoza '299 and Mendoza '231, the AI instrument has a balloon type catheter used to position and seal the dispensing tip of the instrument in the cervix of the animal. The present invention does not use a catheter with a balloon, thus making is less costly to produce. Further, the dispensing tip of the present invention is either positioned at the body of the uterus or in the uterine horns, not the cervix.

In Mendoza '299, the amount of semen diluent is described as being contained in an ampoule, which is a small glass sealed vial. Mendoza '299 never discloses the amount of diluent that is in the ampoule. In Mendoza '231, the patent calls for an optimum total charge of semen and diluting fluid, but no specific amounts are ever disclosed, except that the diluting fluid is in an ampoule.

U.S. Pat. No. 7,056,279 is entitled "Device and Method for Artificial Insemination of Bovines and other Animals". The '279 patent cites Mendoza '231 and describes insemination techniques as follows beginning at column 7, line 12:

> In the classical insemination technique, the straw is thawed and opened at one side and inserted in the insemination instrument. The semen is expelled by moving the cotton plugs forward by means of a stainless steel rod. For the insemination instrument according to the invention, straws can be used. The straws are first thawed at 37° C., during one minute and then the semen (0.25 ml) is then expelled in an ampoule which contains 0.25 ml sodium citrate. The total of 0.5 ml is sufficient for a successful insemination by the deposition of 0.25 ml semen solution for each uterine horn.

The '279 patent teaches that a total of about 1.0 ml of thawed cryopreserved semen and diluent are sufficient for AI of both uterine horns. Further, the '279 patent teaches that this mixture should be deposited near the uterotubal junction (See col. 8, lines 3-8).

Applicant believes that there is still a need for improved AI procedures and apparatus. Specifically, the present invention uses substantially more insemination medium that the aforementioned prior art patents to flood the uterine horns. The present invention does not deposit the insemination medium near the uterotubal junction. Instead, the insemination medium of the present invention is deposited at the body of the uterus or at the posterior of each uterine horn.

U.S. Pat. No. 5,030,202 is for a "Lavage System" The term "lavage" means a therapeutic washing out of an organ or part. This patent applies to animals and in particular to equines (horses). Female horses (mares) sometimes have trouble conceiving immediately after giving birth (foaling). Apparently, part of the difficulty may be retained placenta or infection in the uterus. The uterine lavage apparatus 10 of FIG. 1 includes an inflatable cuff 42 (balloon) better seen in FIG. 2 which is the gravid uterus of a post partum mare. The inflatable cuff 42 is shown in the inflated position in FIG. 2. The cuff 42 is also shown in the inflated position in FIG. 2A which is the nongravid uterus of a mare. This washing technique (lavage) is particularly applicable to post partum mares and is not an artificial insemination procedure.

U.S. Pat. No. 2,566,632 is for an "Artificial Insemination Device". At column 4 line 8, the patent states: "Thus, when the syringe 13 (Referring to FIG. 1) is operated and semen is drawn into the tubing 10, it will flow into the chamber 16 . . . ". "The size of the cavity or dome like chamber 16 may vary but it has been found desirable that this space or chamber have a capacity of about 1 cc. of semen, this being the proper amount for insertion in the animal." Col. 4, lines 23-27. (1 cc equals 1 ml). The semen never enters the bore of the instrument beyond the chamber 16 or the syringe. (Col. 4, lines 55-58). Thus this prior art device uses only a 1 ml dose of semen, contrary to the teaching of the present patent application which recommends that the uterine horns be flooded with insemination medium to better increase the probability of conception. This prior art device does not place the insemination medium in the syringe.

SUMMARY OF THE INVENTION

The invention includes an improved nonsurgical procedure for artificial insemination of bovines. The AI instrument used in the present invention does not use a balloon and is therefore sometimes referred to as "catheter free" or the procedure is referred to as a "catheter free" procedure. The procedure is especially useful with cows that have trouble conceiving and with large or older cows that have enlarged uterine horns. The invention may also lead to breakthroughs in the more widespread use of sex sorted sperm. In the preferred embodiment, the improved procedure uses an insemination medium to flood the uterus with sperm in order to insure that some sperm reaches the tip of the uterine horns, which would improve conception rates. The insemination medium is a mixture of cryopreserved semen that has been thawed and a suitable solution. In the preferred embodiment, the insemination medium is mixed and then injected into the bovine.

In an alternative embodiment, the suitable solution may be injected into the bovine in sufficient volume to flood the uterine horns followed by the semen. Some mixing may occur in the reproductive organs of the bovine. In yet another alternative embodiment, the semen may be injected into the bovine, followed by the suitable solution to flood the uterine horns. Again, some mixing may occur in the reproductive organs of the bovine. However, to ensure thorough mixing of the semen and the suitable solution, Applicant recommends that the insemination medium be mixed prior to injection into the bovine.

The breeder may use a generic solution or they may use one of the specific semen diluents disclosed herein. The frozen semen is thawed and warmed prior to mixture with the solution, which is also warmed.

The invention may be used with or without superovulation. The invention includes a catheter free artificial insemination instrument which may include a syringe connected to a disposable single use pipette. (AI instruments are also sometimes referred to as insemination rods or AI guns.) The procedure for flooding the uterine horns with the insemination medium does not require use of the specific semen diluents disclosed herein or the specific AI instrument also disclosed herein. It is preferable in the practice of this procedure to insert at least a portion of the pipette of the AI instrument to the body of the uterus and concurrently flood both the left and the right uterine horns. Concurrent flooding of both uterine horns is the preferred method because it is generally easier and faster for most clinical personnel to correctly position at least a portion of the pipette of an AI instrument in the body of the uterus, than the posterior of each uterine horn. However, it is also possible for skilled clinical personnel to practice this procedure by insertion of at least a portion of the pipette of the AI instrument into the posterior of one uterine horn to flood that horn and then reposition at least a portion of the pipette of the AI instrument into the posterior of the other uterine horn to flood it in a sequential fashion.

BRIEF DESCRIPTION OF THE DRAWINGS

FIG. 3 is a section view of the AI instrument of the present invention.

FIG. 4 is a section view of a disposable plastic bag for semen diluents.

DETAILED DESCRIPTION OF THE INVENTION

Figure 1:
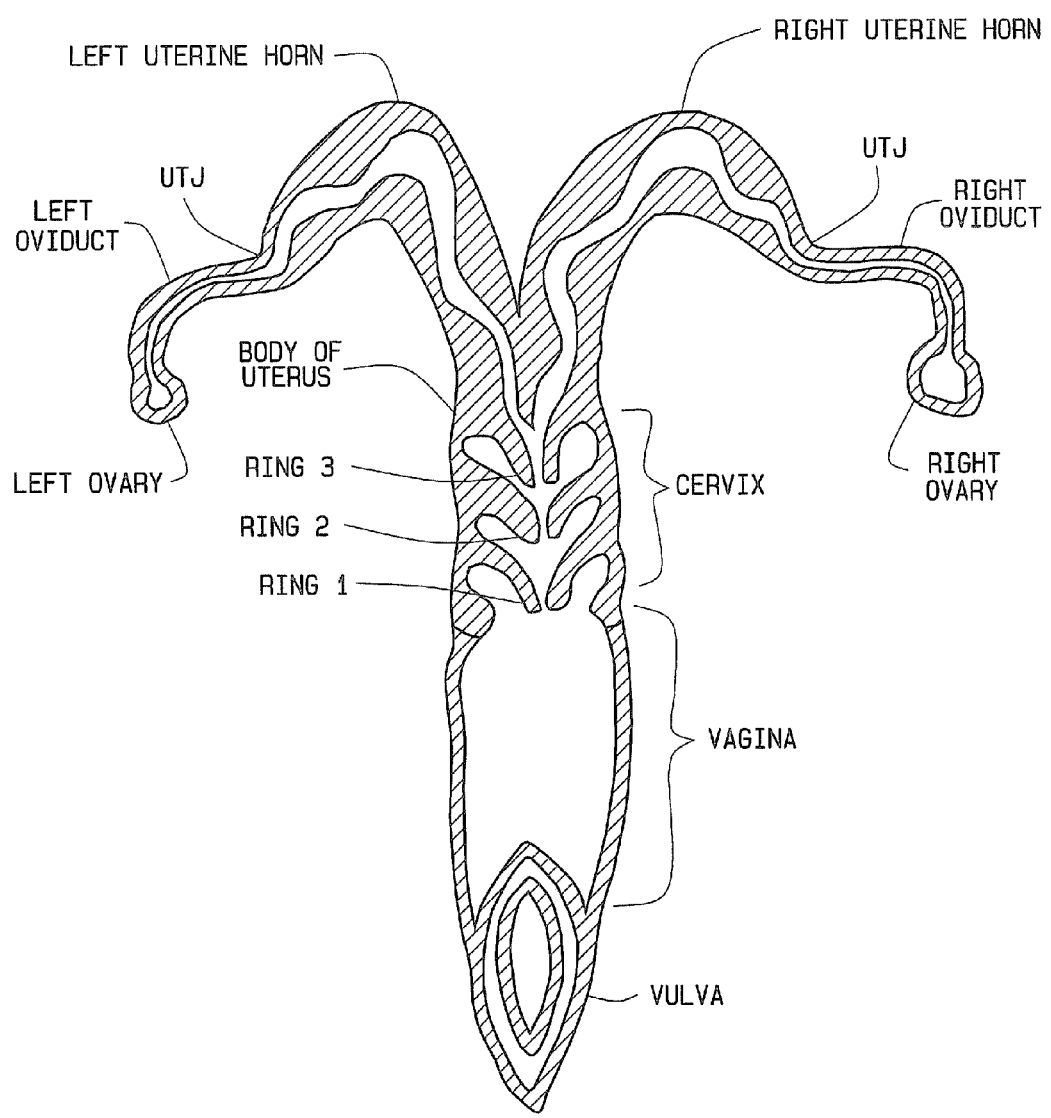
FIG. 1 is a top section view of a cow's reproductive organs.

Conventional artificial reproduction techniques may include hormone injections into the donor cow to induce superovulation with many eggs being released over several hours from both ovaries. These eggs flow into the oviduct.

In the U.S., a cryopreserved straw of semen contains about ½ ml of liquid with about 10-30 million motile sperm. Cryopreserved semen from Canada, Mexico or Europe is often stored in straws containing about ¼ ml of liquid with about 10-30 million motile sperm. These cryopreserved semen straws are kept under liquid nitrogen in tanks and will keep almost indefinitely. When it is time to artificially inseminate a cow, a straw of frozen semen is removed from a liquid nitrogen tank and warmed to about 95° F. (about 35° C.). After thawing, the straw is typically placed directly in an artificial insemination instrument.

The conventional catheter free AI instrument is an elongate metal tube with an elongate metal plunger. The od of the metal tube is about ⅛ inch (about 3 mm) and the overall length is about 18 inches (about 46 cm). The warmed straw of semen is put in the distal end of the conventional AI instrument and the exposed tip of the plastic semen straw is cut off. A plunger is located at the proximal end of the AI instrument.

The cow is restrained in a squeeze shoot or other mechanism. The AI instrument containing the thawed semen straw is then placed in a disposable elongate plastic sheath. The tip of the sheath engages the straw, forming a seal to prevent semen leaks. Sheaths of this design are well know to those skilled in the art and are produced by IMV Technologies of L'Aigle, France (www.imv-technologies.com). The conventional elongate plastic sheath is a single use disposable item. The conventional metal AI instrument is reused repeatedly. The AI instrument and the elongate plastic sheath may then be put in a chemize, which is thin disposable plastic sleeve that fits over the elongate plastic sheath. Use of a chemize is optional in AI procedures. The chemize is more commonly used in ET procedures. (See U.S. Pat. No. 4,453,936 for a description of one type of chemize.)

Using conventional rectal palpation techniques, well known to those skilled in the art, the AI instrument, warmed straw of semen, plastic sheath and optionally a chemize are carefully inserted through the vulva, the vagina, and up to the external cervical os or opening. If a chemise is in place, the AI technician pushes the AI gun and plastic sheath through the chemise. The insemination instrument is then passed through the three fibrous rings in the cervix and into the body of the uterus. The metal plunger is then depressed which ejects the semen from the straw, and through the outlets in the plastic sheath into the body of the uterus. On some occasions, more than one semen straw may be used in a single AI session. If the semen is deposited in the proper location, some of the sperm are transported up both homs of the uterus into the oviducts to hopefully fertilize one or more of the eggs that are present. As previously mentioned, conception occurs in the oviducts. It is easy for inexperienced clinical personnel to improperly position the AI instrument in the cow's reproductive organs. In some cases, the AI procedure is unsuccessful and no eggs are fertilized. Even when successful, sometimes not all of the available eggs are fertilized for several different reasons.

Conventional AI techniques use millions of sperm per insemination whereas a bull deposits billions of sperm each time he mates with a cow or heifer. Further, the bull is not shy repeatedly mating with a cow while she is in heat, further increasing the enormous number of sperm and the large volume of semen in the reproductive system of a cow, while she is in heat. Another problem with conventional AI techniques is that some cows have poor sperm transport mechanisms. Normally, muscles of the uterine horns contract and help push sperm towards the tip of the horns near the oviduct. The junction of the uterine horn and the oviduct is referred to as the uterotubal junction ("UTJ"). At the UTJ is a valve which opens spasmodically to allow a limited amount of sperm into the oviduct.

Figure 2:
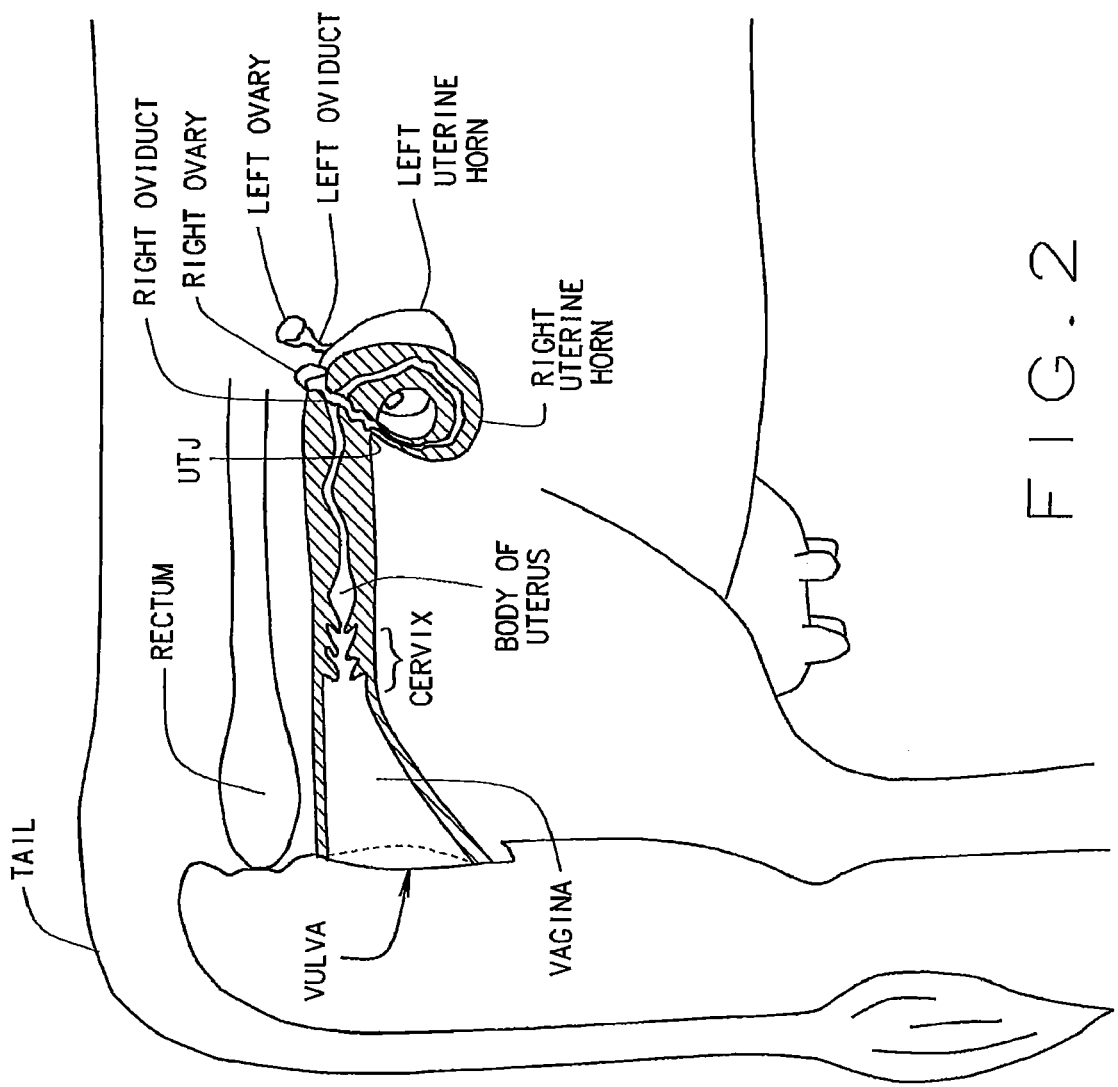
FIG. 2 is a side section view of a cow's reproductive organs.

Referring to FIG. 2, (Which is merely a general representation of the actual organ.) the uterine horns are generally flat and lying in a collapsed state, like a deflated balloon. The interior lining, or endometrium, of the collapsed uterine horns is convoluted.

In the case of embryo transfer, embryo recovery or flushing is generally accomplished through nonsurgical techniques at approximately six to seven days after AI. The donor cow is placed in a squeeze shoot to hold it in place and an epidural block is often given at the tail head.

An embryo flush solution, such as buffered saline, will be used to recover the embryos, if any from the uterine horns. Conventional flushing techniques are typically used with prior art ET procedures and are well know to those skilled in the art, but will be briefly summarized.

A Foley type catheter is connected to a 1 or 2 liter bag of conventional embryo flush solution. A Foley type catheter has a balloon on the distal end to anchor the catheter in place. In the industry the balloon is sometimes referred to as a bladder. Foley type catheters are commonly used after surgery to drain the human bladder. However, the same apparatus is also used in cows in connection with ET techniques. The term "catheter" as used herein refers to a Foley type catheter with an inflatable balloon on the distal end. Term "catheter free" as used herein means that the AI device and/or the AI procedure of the present invention does not utilize an inflatable balloon.

Using conventional ET techniques, a Foley type catheter is carefully inserted through the vulva, the vagina and past the three fibrous rings of the cervix to the body of the uterus. The balloon of the catheter is inflated to anchor the catheter in place. A first clamp is then opened allowing conventional embryo flush solution into the horns of the uterus through the inlet of the catheter. About 20 ml to about 100 ml of embryo flush solution is allowed to flow into the horns of the uterus. The first clamp is closed and a second clamp is opened. Clinical personnel may then gently massage the horns of the uterus using conventional rectal palpation techniques to force the conventional embryo flush solution to drain through the outlet of the catheter into about a 50 micron filter (See U.S. Pat. No. 4,563,172 for example). This process of flushing and draining is repeated until about 1 liter of embryo flush solution has been circulated through the uterus. The conventional embryo flush solution passes through the filter and is discarded. The eggs and embryos, if any are collected in the filter. Conventional embryo flush solution is an off the shelf product and may be purchased from various vendors, including Bioniche Life Sciences, Inc. of Belleville, Ontario, Canada which sells its flush solution under the name "ViGro Complete Flush Solution" (www.bionicheanimalhealth.com). The collected embryos, if any and the unfertilized eggs are typically transferred to a square petri dish for visual screening under a microscope. The live embryos, if any, are then typically transferred to a smaller petri dish. The live embryos may be cryopreserved for future embryo transfer and/or the live embryos may be non-surgically transferred into a recipient cow. Other conventional flushing techniques are described in Canadian Patent 1,073,286 "Apparatus for Use in Collecting Eggs from Animals".

Referring now to FIG. 1, the reproductive organs of a female bovine are shown in top section view and referring to FIG. 2, the reproductive organs are shown in side section view. The vulva is the external opening to the vagina. The cervix has three fibrous annular rings that are tightly contracted, except when the bovine is in heat. When the bovine comes into heat, the three rings relax allowing sperm easier passage into the uterus. Sperm is then deposited by a bull into the vagina and is transported through the cervix into the body of the uterus. During AI even though the three fibrous rings are relaxed it can often be difficult for clinical personnel to pass an AI instrument through the cervix and position the tip properly in the body of the uterus.

In a natural (non-superovulated) setting one egg is released from the left or right ovary and it travels down the respective oviduct. When a cow releases a single egg, she is sometimes referred to as a "single ovulating" female bovine. When a bull breeds a bovine in a natural setting, some of the sperm are transported up the uterine horns to the oviduct to fertilize the egg. If egg is fertilized it lingers in the oviduct for about 4 days and then migrates into the uterine horn. The embryo begins implanting in the uterine horn about 15 days after conception.

Some prior art AI techniques deposit a quarter to a half ml of thawed cryopreserved semen in the body of the uterus. U.S. Pat. No. 7,056,279 teaches that a total of about 1.0 ml of thawed cryopreserved semen and diluent are sufficient for AI of both uterine horns. After conventional AI, the sperm must then be transported up the collapsed and convoluted uterine horns to the oviduct to hopefully fertilize one or more eggs, if the bovine has been superovulated. The number of cryopreserved sperm used in prior art AI procedures is millions compared with a bull which ejaculates billions. Further, in a natural setting, a bull ejaculates about 5-15 ml of semen per intercourse. The AI procedure of the present invention is designed to overcome some of the limitations of prior art AI techniques by mixing the quarter or half ml of cryopreserved semen with a comparatively large amount of suitable solution that will keep the sperm alive and flood the uterine horns. The mixture of semen and a suitable solution is referred to at the insemination medium. Some prior art procedures do not mix the cryopreserved semen in the straw with any solution or diluent after the semen straw has been thawed for AI. Other prior art procedures mix the thawed cryopreserved semen with about 0.5 ml of diluent. The insemination medium, of the present invention is used in comparatively larger volumes to flood the uterine horns with motile sperm.

Referring to FIG. 3, the AI instrument of the present invention is shown in section view and generally referred to by the numeral 10. Unlike the AI device disclosed in Mendoza '229 or '231, the AI instrument of the present invention does not use a balloon to anchor the instrument, prior to the introduction of the insemination medium into the bovine. The AI instrument 10 of the present invention is sometimes referred to as "catheter free" because it does not have a balloon on the distal end. Likewise, the procedure of the present invention is sometimes referred to as a "catheter free" procedure because there is no balloon to be inflated or deflated during the procedure.

The AI instrument 10 includes a single use disposable, hollow pipette 12 which is formed from semirigid plastic to facilitate insertion through the reproductive organs of a female bovine. The pipette has a proximal end 14 and a distal end 16. The pipette is about 18 inches to about 20 inches long. For older larger cows, a pipette of 22 inches may even be appropriate. The internal diameter of the elongate passageway 17 is about ⅛ inch and the outside diameter of the pipette is about 7/32 inch. However, the exact dimensions of the AI instrument are not critical to this invention. What is important is that the AI instrument be able to pass through the bovine reproductive organs to at least the body of the uterus and be able to hold a sufficient volume of insemination medium to flood the uterine horns. The distal end 16 has a smooth rounded tip 18 surrounding the outlet 19 to avoid damage to the bovine when the pipette is inserted into the reproductive organs.

A syringe 20 is connected to the pipette 12 by a connector 22. The syringe may also be generally referred to as a fluid supply reservoir. Other fluid supply reservoirs, know to those skilled in the art, such as a squeeze bulb, are within the scope of this invention, provided that they can hold a sufficient volume of insemination medium to flood the horns of the uterus of the cow in question. The connector 22 may be a separate member. In the alternative, the connector 22 may be formed as a part of the pipette or the syringe. The syringe includes a cylindrical body 24 with a dispensing tip 26 on one end and finger tabs 28 on the other end. A piston 30 is sized and arranged to slide in the cylindrical syringe body 24. On one end of the piston is an elastomeric circular seal 32 and on the other end is a thumb tab 34. The circular seal, the cylindrical body and the dispensing tip define a solution chamber 36 holding at least a sufficient volume of insemination medium for the cow in question. The solution chamber 36 is in fluid communication with the elongate passageway 17 of the pipette 12.

In FIG. 3, the insemination medium has been drawn into the solution chamber 36 of the syringe. When the thumb tab 34 is depressed, the seal 32 slides down the syringe body 24 towards the dispensing tip 26. This pumping action forces the insemination medium through the connector 22, through the elongate passageway 17 of the pipette and out the outlet 19.

One formula for a suitable semen diluent is as follows:
3.187 grams tris (trishydroxymethylaminomethane)
1.781 grams citric acid
1.136 grams fructose
80 ml distilled water The pH of this tris-fructose-citric acid solution is about 7 to about 7.2 and the osmolarity is about 285 mOsm/L. Other suitable solutions may be used in this the practice of this invention provided that they are compatible with the sperm and semen. Some extenders used in cryopreservation may be a suitable solution for the practice of this invention and others may not. For example, Triladyl, a common extender used in cryopreservation of semen is not a suitable solution for use in the practice of this invention because it also contains the cryoprotectant glycerol which will kill sperm. The semen diluent disclosed in U.S. Pat. No. 6,368,786 (assigned to IMV Technologies) also contains glycerol which means that it is likewise not suitable for use in this invention. Other extenders such as Biladyl®, Fraction A, also from Minitube, does not contain a cryoprotectant or glycerol and may be suitable in the practice of this invention. An embryo flush solution such as ViGro Complete Flush Solution may also be used as a semen diluent. Other products and solutions such as a saline solution may also be suitable provided they have a proper pH, osmolarity and are properly buffered to dilute and support the life of the sperm.

The semen diluents and/or other suitable solutions may be conveniently premixed in volumes of 5 ml, 10 ml, 20 ml, or 40 ml and thereafter may easily be contacted with the semen to prepare the insemination medium. The amount of insemination medium will depend on the size of the uterine horns of the bovine that is being artificially inseminated. A sufficient volume of insemination medium should be used to flood both uterine horns. The uterine horns may be flooded concurrently, which is the preferred procedure or sequentially depending on the experience level of the AI technician. Both procedures are within the scope of this invention. The volume of insemination medium can be estimated from the general body size of the cow and/or rectal palpation of the horns prior to injection of the insemination medium. The term "sufficient volume" of insemination medium may also be referred to as an "effective amount" or a "fertility enhancing amount".

The size of uterine horns varies from relatively small horns in a virgin heifer to large uterine horns in older cows that have produced several calves. As a general rule, cows weighing less than 1000 pounds will have small uterine horns and from about 2 ml to about 50 ml and preferably about 10 ml of insemination medium should do a good job of flooding the uterine horns and is a fertility enhancing amount. In some virgin heifers, a sufficient volume of insemination medium may be as little as about 2 ml to about 20 ml an preferably about 5 ml. Insemination medium is relatively inexpensive and larger volumes are more likely to result in conception than smaller volumes. Applicant recommends using larger volumes, but the aforementioned smaller volumes are also within the scope of this invention.

As a general rule, cows weighing from about 1000 to about 1,400 pounds will have medium sized uterine horns and from about 2 ml to about 50 ml and preferably about 20 ml of insemination medium should do a good job of flooding the uterine horns and is a fertility enhancing amount. As a general rule, cows weighing more than about 1,400 pounds will typically have larger uterine horns and be older dairy and beef cattle. From about 2 ml to about 50 ml and preferably about 40 ml of insemination medium should do a good job of flooding the uterine horns and is a fertility enhancing amount for cows weighing over 1,400 pounds. There are exceptions to these general guidelines as discussed above.

Referring now to FIG. 4, a section view of a disposable plastic bag 50 for semen diluents is shown. The bag 50 defines a solution chamber 52 which holds the semen diluents 54. The bag further defines an outlet 56 with an outlet port 58. The outlet port 0058 may be sealed with a cap 60 or it may be sealed with a needle septum, not shown, for penetration with a needle. Another alternative is a spike port, not shown. The dispensing tip 26 of the syringe may be sized and arranged to engage the outlet port 58 to facilitate filling of the solution chamber of the syringe with semen diluents from the bag 50. The dispensing tip may alternatively be fitted with a connector such as a luer lock, not shown, to connect the syringe to a needle. The type of solution connection between the bag 50 and the syringe 20 is not critical to the practice of this invention, provided that the connection does not leak.

Figure 5:
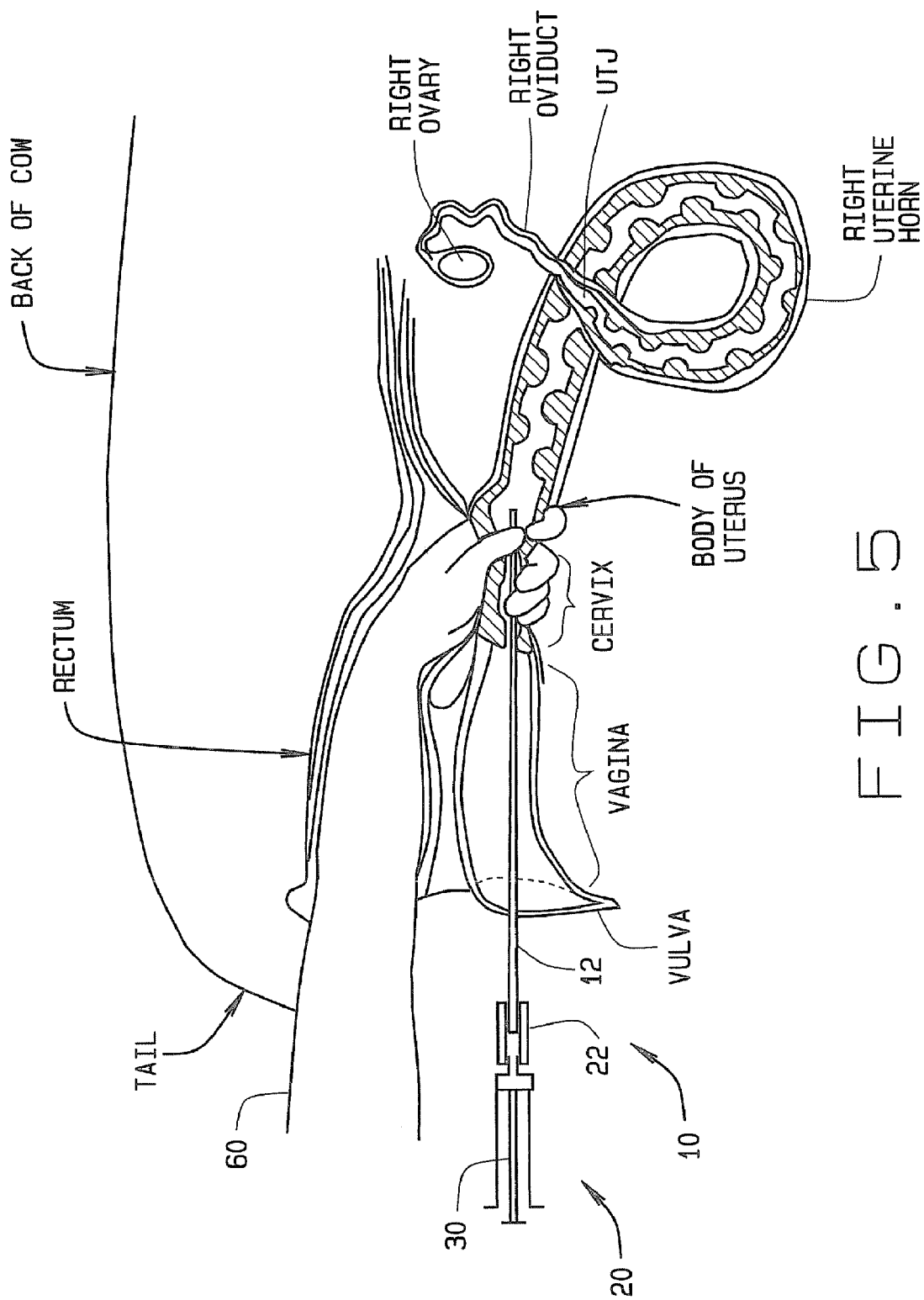
FIG. 5 is a side section view of a cow's reproductive organs showing only the right uterine horn. A person's arm is inserted into the rectum for rectal palpation of the reproductive organs. The AI instrument of FIG. 3 has been inserted to the body of the uterus and the uterine horns have been flooded with insemination medium.

The artificial breeding procedure of the present invention is as follows. At least one straw of cryopreserved semen is warmed to a suitable temperature, about 95° F. And preferably, a plastic bag of semen diluent is likewise warmed to a suitable temperature, which is also about 95° F. The warmed semen and the warmed semen diluent are mixed together forming an insemination medium which is drawn into the solution chamber 36 of the syringe 20 or other suitable fluid supply reservoir of an artificial insemination instrument. Another type of suitable supply reservoir is a fluid holding container that may be connected to a fluid pump. The disposable pipette 12 is removed from a delivery bag, not shown, and connected to the connector 22. The insemination medium is pumped to the orifice 19 in the pipette. One arm 60 of a person is inserted into the rectum of the bovine for rectal palpation of the bovine's reproductive organs, as shown in FIG. 5. Specifically, the hand is used to palpate the cervix, as shown in FIG. 5 to carefully guide the AI instrument through the three fibrous rings of the cervix.

The AI instrument 10 of FIG. 3 is gently inserted through the vulva, the vagina, and the cervix, to the body of the uterus in order to concurrently flood both uterine horns. As shown in FIG. 2, the uterine horns are normally in a generally flat, condition in the body of the bovine presenting a convoluted physical organ for the sperm to traverse. In contrast, in FIG. 5, the right uterine horn and the left uterine horn, not shown, have been concurrently flooded making it much easier for the sperm to be mechanically transported to the UTJ near the oviduct. In FIG. 5, the size of the uterine horns has been exaggerated and enlarged in the drawing for illustrative purposes.

In the alternative, each uterine horn may be sequentially flooded with insemination medium. To sequentially flood each horn, the tip 18 of the pipette should be inserted into the horn, beyond the body of the uterus. This position is not shown in the drawings. The right uterine horn is flooded first, and then the pipette is relocated to the left uterine horn. Additional insemination medium is injected to flood the left uterine horn, not shown. The AI instrument and the pipette are then removed. Or the left horn may be flooded first and then the right horn. The order of the sequence is not important. Sequential flooding of each uterine horn is believed to be slower and more difficult than concurrent flooding, because the pipette must be relocated from one horn to the next. However, cows with an extremely short uterine body may benefit more from sequential horn flooding to insure that the insemination medium reaches both horns, which could increase conception rates. Both concurrent and sequential flooding are within the scope of this invention.

Some prior art techniques use only ¼ to ½ ml of cryopreserved semen for artificial insemination which is only a small amount of fluid (Only a few drops). Other prior art techniques as taught in U.S. Pat. No. 7,056,279 mix ¼ ml of cryopreserved semen with about ¼ ml of diluent per uterine horn. Accordingly, the prior art technique in U.S. Pat. No. 7,056, 279 injects ½ ml of semen and ½ ml of diluent for a total of 1 ml of insemination medium into the bovine. One ml of insemination medium does not flood the uterine horns. In contrast, the present invention uses a large volume of insemination medium to flood the horns of the uterus. For example, in the case of sex sorted sperm for a virgin heifer, preferably about 5 ml of suitable solution is mixed with ¼ ml of cryopreserved sex sorted semen, which is about 10 times more diluent than some prior art AI techniques. In the case of non-sex sorted sperm for cows that have given birth to their first calf, preferably about 10 ml of suitable solution is mixed with ½ ml of cryopreserved semen, which is about 20 times more diluent than some prior art AI techniques. This invention makes it easier for the sperm to be mechanically transported through the uterine horns to the oviduct, thus improving conception rates, especially in cows with larger fertilization. All of these unfertilized oocytes, dead embryos, and live embryos (collectively known and ova) are flushed from the cow with a liter or more of embryo flush solution (Embryo flush solution is sometimes also referred to as recovery solution, in the industry). Each live embryo that is recovered is either transferred fresh into a recipient cow or cryopreserved to be transferred later into a recipient cow. The recipient cow is a surrogate mother, used for development of the fertilized embryo, birth and rearing of the calf. The recipient cow is typically less expensive than the genetically valuable donor cow from which the embryos are harvested.

As previously mentioned, a cow in a natural setting with a life span of 10 years may produce about 7 calves over her lifetime. Using conventional procedures of embryo transfer, a donor cow with a life of 10 years may produce as many as 20 to 40 calves over her lifetime, with the help of multiple recipient cows.

AI produces conception rates of about 50 to 70% in beef cattle, but only about 25% in dairy cattle. There is still room for improvement of artificial breeding techniques to improve rates of conception and therefore increase the total number of calves that a valuable donor cow can produce over her lifetime.

U.S. Pat. No. 5,147,229 to Mendoza is for a "Device to Facilitate Artificial Insemination of Bovines and Similar Animals". As shown in Mendoza '229 at FIGS. 2 and 9, the AI instrument with an expanding balloon 2 is used to anchor the tip of the artificial insemination device in the cervix to create a seal. U.S. Pat. No. 6,071,231 to Mendoza is an improvement on Mendoza '229 and is for another insemination instrument with a balloon catheter as best seen in FIGS. 4-6. In Mendoza '231, at Column 2, beginning at line 5, the device is described as follows:

> In operation, the frozen semen sample in a common plastic semen storage straw . . . is warmed and mixed with diluting fluid contained in an ampoule.

reproductive tracts, cows being inseminated with sex sorted semen, cows being inseminated with low motility semen, cows that are classified s problem breeders, superovulated cows and for cows being inseminated by inexperienced AI technicians who may not be placing semen in the precise location.

The semen diluents disclosed herein are recommended for the practice of this invention but any biologically suitable solutions and other semen diluents, not disclosed herein may be used with this procedure to flood the horns of the uterus with an insemination medium, thus making it easier for the sperm to reach the UTJ and the oviduct. This procedure may be practiced with any semen diluents or other suitable solution that is compatible with the sperm and semen. Further, this procedure may be used with any AI instrument that facilitates proper placement and discharge of the insemination medium to flood the uterine horns, either concurrently or sequentially.

A first alternative procedure for practice of this invention is described below. A semen diluent or other suitable solution is first injected into the body of the uterus in a sufficient volume to flood the uterine horns. Then one or more thawed straws of semen are injected into the body of the uterus to mix with the semen diluent or other suitable solution inside the reproductive organ's of the cow. In the alternative, one or more thawed straws of semen could be injected into the body of the uterus followed by injection of a semen diluent or other suitable solution in sufficient volume to flood the uterine horns. It is preferred to mix the semen with the semen diluent or other suitable solution prior to injection into the cow, but this alternative procedure may also increase conception rates and be a suitable in the practice of this invention.

A second alternative procedure for practice of this invention is described below. A semen diluent or other suitable solution is first injected into one horn of the uterus in a sufficient volume to flood that uterine horn. Then one or more thawed straws of semen are injected into the aforementioned uterine horn to mix with the semen diluent or other suitable solution inside the reproductive organ's of the cow. A semen diluent or other suitable solution is injected into the opposite horn of the uterus in sufficient volume to flood that uterine horn. Then one or more thawed straws of semen are injected into the opposite uterine horn to mix with the semen diluent or other suitable solution inside the reproductive organ's of the cow. Again, it is preferred to mix the semen with the semen diluent or other suitable solution prior to injection into the cow, but this alternative procedure may also increase conception rates.

The sex of mammals is determined by the chromosomes in the sperm, not the egg. Various segments of the cattle industry have recently found that it is valuable to use sex sorted sperm for AI in order to predetermine the sex of offspring. The sex of sperm is sorted in the dairy cattle industry to insure that a larger percentage of females will be born considering that males will not produce milk. The sex of sperm is sorted in the beef cattle industry because males better utilize feed and ultimately put on more weight than females.

Producers of sex sorted sperm currently recommend that it only be used to artificially inseminate a virgin heifer, and not more mature cows. This recommendation is based on at least two reasons. First, the uterine horns of virgin heifers are small making the physical transportation of inseminated sperm from the uterus to the oviduct more likely with only a ¼ ml straw of semen. Second there are only about 2 million sex sorted sperm packaged in a ¼ ml straw of semen, compared with 20-30 million sperm in a non-sex sorted ½ ml straw of semen. This self imposed industry wide recommendation to use sex sorted sperm on virgin heifers drastically limits the market for sex sorted sperm. Applicant believes that the present invention using the aforementioned AI flooding technique will allow sex sorted semen to be used with cows in general, and not just virgin heifers. This may dramatically increase the market for sex sorted sperm in the cattle industry. The term semen as used herein includes both unsorted sperm and sex sorted sperm. The term sex sorted sperm as used herein is limited to sex sorted sperm.

The invention claimed is:

1. A catheter free nonsurgical procedure for artificial insemination of a single ovulating female bovine, having a vulva, a vagina, a cervix, a left and a right uterine horn, the procedure comprising the following steps:
    estimating the approximate size of the single ovulating female bovine;
    filling at least a portion of a fluid supply reservoir with from about 2 ml to about 50 ml of an insemination medium depending on the estimated size of the single ovulating female bovine;
    using rectal palpation to insert at least a portion of a pipette through the vulva, the vagina, and the cervix to at least the body of the uterus; and
    injecting the insemination medium through the pipette in sufficient volume to flood the uterine horns of the single ovulating female bovine.

2. The procedure of claim 1 wherein the volume of insemination medium for a single ovulating female bovine weighing less than about 1000 pounds is preferably 10 ml.

3. The procedure of claim 1 wherein the volume of insemination medium for a female single ovulating bovine weighing from about 1000 to about 1,400 pounds is preferably about 20 ml.

4. The procedure of claim 1 wherein the volume of insemination medium for a single ovulating female bovine weighing more than about 1,400 pounds is preferably about 40 ml.

5. The procedure of claim 1 wherein the insemination medium is a mixture of a suitable solution and cryopreserved sex sorted sperm that has been thawed.

6. A catheter free nonsurgical procedure for artificial insemination of a single ovulating female bovine having reproductive organs, the procedure comprising:

estimating the approximate weight of the single ovulating female bovine;

contacting thawed cryopreserved semen with a suitable solution to form an insemination medium;

selecting an effective amount of the insemination medium for the single ovulating female bovine based on the estimated weight of the single ovulating female bovine; and using rectal palpation to injecting an effective amount of the insemination medium into the reproductive organs of the single ovulating female bovine to flood the uterine horns.

7. The procedure of claim 6 wherein the single ovulating female bovine has a left uterine horn and a right uterine horn and the insemination medium is injected into a body of the uterus to flood both uterine horns concurrently.

8. The procedure of claim 6 wherein the single ovulating female bovine has a left uterine horn and a right uterine horn and each uterine horn is flooded sequentially with the insemination medium.

9. The procedure of claim 6 wherein the insemination medium is a mixture of a suitable solution and cryopreserved sex sorted sperm that has been thawed.

10. A catheter free nonsurgical procedure for artificial insemination of a single ovulating virgin heifer having reproductive organs including left and right uterine horns, the procedure comprising the following steps:
mixing thawed cryopreserved semen with a suitable solution to form an insemination medium;
placing from about 2 ml to about 20 ml of the insemination medium in an artificial insemination instrument including a fluid supply reservoir and a pipette;
using rectal palpation to insert at least a portion of the pipette into the reproductive organs of the single ovulating virgin heifer; and
injecting the insemination medium from the fluid supply reservoir through the pipette into the reproductive organs of the single ovulating virgin heifer to flood the uterine horns of the single ovulating virgin heifer.

11. The procedure of claim 10 wherein the fluid supply reservoir is a syringe.

12. The procedure of claim 10 wherein the uterine horns are flooded concurrently.

13. The procedure of claim 10 wherein the uterine horns are flooded sequentially.

14. The procedure of claim 10 wherein the amount of the insemination medium is preferably 5 ml.

15. A catheter free nonsurgical procedure for artificial insemination of a single ovulating virgin heifer having reproductive organs including left and right uterine horns, the procedure comprising the following steps:
mixing ¼ml of thawed cryopreserved sex sorted sperm with about 5 ml of a suitable solution to form an insemination medium;
placing the insemination medium in an artificial insemination instrument;
using rectal palpation to insert at least a portion of the artificial insemination instrument into the reproductive organs of the single ovulating virgin heifer; and
injecting the insemination medium from the artificial insemination instrument into the reproductive organs of the single ovulating virgin heifer in an effective amount to flood the uterine horns of the single ovulating virgin heifer.

16. The procedure of claim 15 wherein the suitable solution is a semen diluent.

17. A catheter free nonsurgical procedure for artificial insemination of a superovulated female bovine, having a vulva, a vagina, a cervix, a left and a right uterine horn, the procedure comprising the following steps:
estimating the approximate size of the superovulated female bovine;
filling at least a portion of a fluid supply reservoir with an insemination medium based on the estimated size of the superovulated female bovine, the insemination medium containing thawed cryopreserved semen and a suitable solution;
using rectal palpation to insert at least a portion of a pipette through the vulva, the vagina, and the cervix to at least the body of the uterus; and
injecting from about 2 to about 50 ml of the insemination medium through the pipette in sufficient volume to flood the uterine horns of the superovulated female bovine.

18. The procedure of claim 17 wherein the volume of insemination medium for a superovulated female bovine weighing about 1000 pounds or less is preferably 10 ml.

19. The procedure of claim 17 wherein the volume of insemination medium for a superovulated female bovine weighing from about 1000 to about 1,400 pounds is preferably about 20 ml.

20. The procedure of claim 7 wherein the volume of insemination medium for a superovulated female bovine weighing about 1,400 pounds or more is preferably about 40 ml.

* * * * *